(12) United States Patent
Haywood (10) Patent No.: US 10,588,566 B2
(45) Date of Patent: Mar. 17, 2020

(54) ABLATION CONDITION DETERMINATION METHODS AND SYSTEMS

(71) Applicant: UNIVERSITY HOSPITALS PLYMOUTH NATIONAL HEALTH SERVICE TRUST, Devon (GB)

(72) Inventor: Guy Haywood, Plymouth (GB)

(73) Assignee: UNIVERSITY HOSPITALS PLYMOUTH NATIONAL HEALTH SERVICE TRUST, Devon (GB)

( * ) Notice: Subject to any disclaimer, the term of this patent is extended or adjusted under 35 U.S.C. 154(b) by 142 days.

(21) Appl. No.: 15/379,187

(22) Filed: Dec. 14, 2016

(65) Prior Publication Data
US 2018/0160969 A1 Jun. 14, 2018

(51) Int. Cl.
*A61B 5/04* (2006.01)
*A61B 5/00* (2006.01)
(Continued)

(52) U.S. Cl.
CPC .......... *A61B 5/4848* (2013.01); *A61B 5/0245* (2013.01); *A61B 5/687* (2013.01);
(Continued)

(58) Field of Classification Search
CPC .... A61B 18/1492; A61B 5/046; A61B 5/0464
See application file for complete search history.

(56) References Cited

U.S. PATENT DOCUMENTS 4,640,298 A * 2/1987 Pless ................... A61B 5/0422
607/124
5,431,696 A * 7/1995 Atlee, III ............ A61N 1/0517
600/374
(Continued)

FOREIGN PATENT DOCUMENTS

WO WO-2006/010908 A1 2/2006

OTHER PUBLICATIONS

Verma A., Jiang C-Y., Betts Tr., Chen J., Deisenhofer I., Mantovan R., et al. "Approaches to Catheter Ablation for Persistent Atrial Fibrillation." *New England Journal of Medicine.* vol. 372, part 19, May 2015, pp. 1812-1822.
(Continued)

*Primary Examiner* — Michael J D Abreu
(74) *Attorney, Agent, or Firm* — Marshall, Gerstein & Borun LLP (57) ABSTRACT

A method and apparatus are disclosed for determining if a previously carried out heart ablation has been effective in isolating tissue. The method involves inserting an esophageal device, e.g. a catheter, into the esophagus so that an electrode is adjacent the heart, pacing the electrode with an electrical pacing signal, and determining if the heart adopts the pacing signal. Adoption of the pacing signal is indicative of the tissue not being electrically isolated by the ablation, and so may signal that a re-ablation procedure is necessary. Non adoption of the pacing signal is indicative of the tissue being electrically isolated by the ablation. Also disclosed is a processing unit for comparing a measured heart signal with a predetermined pacing signal to determine heart adoption of the pacing signal. The device and processing unit may be used to measure natural heart signals in the esophagus to assist in correct catheter positioning.

14 Claims, 4 Drawing Sheets

(51) Int. Cl.
| | |
|---|---|
| A61B 5/0245 | (2006.01) |
| A61B 18/14 | (2006.01) |
| A61N 1/05 | (2006.01) |
| A61N 1/362 | (2006.01) |
| A61N 1/00 | (2006.01) |
| A61B 6/12 | (2006.01) |
| A61B 18/00 | (2006.01) |
| A61B 8/08 | (2006.01) |
| A61B 8/12 | (2006.01) |
| A61B 90/00 | (2016.01) |

(52) U.S. Cl.
CPC ........ *A61B 5/6852* (2013.01); *A61B 18/1492* (2013.01); *A61N 1/00* (2013.01); *A61N 1/0517* (2013.01); *A61N 1/362* (2013.01); *A61B 5/04012* (2013.01); *A61B 6/12* (2013.01); *A61B 8/0883* (2013.01); *A61B 8/12* (2013.01); *A61B 2018/00357* (2013.01); *A61B 2018/00488* (2013.01); *A61B 2018/00577* (2013.01); *A61B 2018/00839* (2013.01); *A61B 2018/1467* (2013.01); *A61B 2090/3782* (2016.02)

(56) References Cited

U.S. PATENT DOCUMENTS

| | | | |
|---|---|---|---|
| 6,532,388 B1* | 3/2003 | Hill | A61N 1/0517 607/2 |
| 8,145,289 B2 | 3/2012 | Calabro' et al. | |
| 2004/0059237 A1* | 3/2004 | Narayan | A61B 5/04525 600/509 |
| 2006/0106375 A1* | 5/2006 | Werneth | A61B 18/1492 606/32 |

OTHER PUBLICATIONS

Wynn GJ., Das M., Bonnett LJ., Panikker S., Wong T., Gupta D. "Efficacy of Catheter Ablation for Persistent Atrial Fibrillation: A Systematic Review and Meta-Analysis of Evidence From Randomized and Nonrandomized Controlled Trials." *Circulation: Arrhythmia and Electrophysiology.* American Heart Association, Inc. vol. 7, part 5, Aug. 2014, pp. 841-852 and Supplemental Material.

Wynn GJ., El-Kadri M., Haq I, Das M., Modi S., Snowdon R., et al. "Long-Term Outcomes After Ablation of Persistent Atrial Fibrillation: An Observational Study Over 6 Years." *Open Heart* 2016;3:e000394. Doi:10.1136/openhrt-2015-000394. Published Jul. 26, 2016.

Todd DM., Skanes AC., Guiraudon G., Guiraudon C., Krahn AD., Yee R, et al. "Role of the Posterior Left Atrium and Pulmonary Veins in Human Lone Atrial Fibrillation: Electrophysiological and Pathological Data From Patients Undergoing Atrial Fibrillation Surgery." *Circulation.* American Heart Association, Inc. vol. 108, part 25, Dec. 2003, pp. 3108-3114.

O'Neill L., Hensey M., Nolan W., Keane D. "Clinical Outcome When Left Atrial Posterior Wall Box Isolation is Included as a Catheter Ablation Strategy in Patients With Persistent Atrial Fibrillation." *Journal of Interventional Cardiac Electrophysiology: An International Journal of Arrhythmias and Pacing. Journal of Interventional Cardia Electrophysiology.* vol. 44, part 1, Oct. 2015, pp. 63-70.

He X., Zhou Y., Chen Y., Wu L., Huang Y., He J. "Left Atrial Posterior Wall Isolation Reduces the Recurrence of Atrial Fibrillation: A Meta-Analysis." *Journal of Interventional Cardiac Electrophysiology: An International Journal of Arrhythmias and Pacing.* vol. 46, part 3, Sep. 2016, pp. 267-274.

Bisleri G., Rosati F., Bontempi L., Curnis A., Muneretto C. "Hybrid Approach for the Treatment of Long-Standing Persistent Atrial Fibrillation: Electrophysiological Findings and Clinical Results." *European Journal of Cardio-Thoracic Surgery.* vol. 44, part 5, Mar. 8, 2013, pp. 919-923.

Badhwar V., Rankin JS., Damiano RJ., Gillinov AM., Bakaeen FG., Edgerton JR., et al. "The Society of Thoracic Surgeons 2017 Clinical Practice Guidelines for the Surgical Treatment of Atrial Fibrillation." *The Annals of Thoracic Surgery.* vol. 103, part 1, Jan. 2017, pp. 329-341.

Cury RC., Abbara S., Schmidt S., Malchano ZJ., Neuzil P., Weichet J., et al. "Relationship of the Esophagus and Aorta to the Left Atrium and Pulmonary Veins: Implications for Catheter Ablation of Atrial Fibrillation." *Heart Rhythm.* vol. 2, part 12, Dec. 2005, pp. 1317-1323.

Jenkins JM., Dick M., Collins S., O'Neill W., Campbell RM., Wilber DJ. "Use of the Pill Electrode for Transesophageal Atrial Pacing." *Pacing and Clinical Electrophysiology.* vol. 8, part 4, Jul.-Aug. 1985, pp. 512-527.

Twidale N., Roberts-Thomson P., Tonkin AM. "Transesophageal Electrocardiography and Atrial Pacing in Acute Cardiac Care: Diagnostic and Therapeutic Value." *Australian and New Zealand Journal of Medicine.* vol. 19, part 1, Feb. 1989, pp. 11-16.

Arzbaecher R., Jenkins JM. "A Review of the Theoretical and Experimental Bases of Transesophageal Atrial Pacing." *Journal of Electrocardiology.* vol. 35, part 4B, Oct. 2002, pp. 137-141.

Sra J., Krum D., Malloy A., Bhatia A., Cooley R., Blanck Z., et al. "Posterior Left Atrial-Esophageal Relationship Throughout the Cardiac Cycle." *Journal of Interventional Cardiac Electrophysiology.* vol. 16, part 2, Aug. 2006, pp. 73-80.

Tsao H-M., Wu M-H., Higa S., Lee K-T., Tai C-T., Hsu N-W., et al. "Anatomic Relationship of the Esophagus and Left Atrium: Implication for Catheter Ablation of Atrial Fibrillation." *CHEST Journal.* vol. 128, part 4, Oct. 2005, pp. 2581-2587.

Müller P., Dietrich J-W., Halbfass P., Abouarab A., Fochler F, Szöllösi A, et al. "Higher Incidence of Esophageal Lesions After Ablation of Atrial Fibrillation Related to the Use of Esophageal Temperature Probes." *Heart Rhythm.* vol. 12, part 7, Jul. 2015, Abstract only.

Knecht S., Sticherling C., Reichlin T., Mühl A., Pavlović N., Schaer B., et al. "Reliability of Luminal Oesophageal Temperature Monitoring During Radiofrequency Ablation of Atrial Fibrillation: Insights From Probe Visualization and Oesophageal Reconstruction Using Magnetic Resonance Imaging." *Europace* euw129, Jun. 29, 2016, Abstract only.

Villain E, Boudjemline Y, Bonnet D. "Emergency Trans-Oesophageal Ventricular Pacing in a Child." *Cardiology in the Young.* vol. 14, part 3, Jun. 2004, pp. 333-334.

Gallagher JJ, Smith WM, Kerr CR, Kasell J, Cook L, Reiter M, et al. "Esophageal Pacing: A Diagnostic and Therapeutic Tool." *Circulation.* vol. 65, part 2, Feb. 1982, pp. 336-341.

Haeberlin A., Niederhauser T., Marisa T., Mattle D., Jacomet M., Goette J., et al. "Esophageal Long-Term ECG Reveals Paroxysmal Atrial Fibrillation." *Circulation.* vol. 125, part 18, May 2012, pp. 2281-2282.

Haeberlin A, Lacheta L, Niederhauser T, Marisa T, Wildhaber RA, Goette J, et al. "Markers for Silent Atrial Fibrillation in Esophageal Long-Term Electrocardiography." *Journal of Electrocardiology.* vol. 49, part 4, Jul.-Aug. 2016, pp. 496-503.

Esotest Esophageal Temperature Monitoring System. Advertisement [online]. FIAB SpA, 2015 [retrieved from internet on Nov. 29, 2016]. Retrieved from Internet: <URL: <http://www.fiab.it/en/download.php?filepath=admin/cataloghi/esotest_eng.pdf>>.

* cited by examiner

ABLATION CONDITION DETERMINATION METHODS AND SYSTEMS

FIELD OF THE DISCLOSURE

The present disclosure relates to determining the condition of an ablation. The disclosure more particularly pertains to methods and apparatuses for determining whether a previous procedure to ablate the heart walls has been effective.

BACKGROUND OF THE DISCLOSURE

Cardiac arrhythmias such as atrial fibrillation or focal atrial tachycardia affect a significant amount of the population. It is estimated that between 1 and 1.5% of the world's population are affected by atrial fibrillation. 25% of people aged 40 or older will develop atrial fibrillation. The heart condition is caused by disordered electrical activity in the atrial chambers of the heart. Symptoms of atrial fibrillation include shortness of breath, palpitations, dizziness, light-headedness, chest pain, chest discomfort, fatigue, anxiety, depression and increased side effects from drugs. Furthermore, it is estimated that atrial fibrillation causes 20-30% of all strokes and increases the risk of strokes by a factor of 5 compared to those without atrial fibrillation.

There are several known methods for treating atrial fibrillation. Some drugs have been found to reduce the symptoms, although the effectiveness of such drugs is variable and such drugs also exhibit side effects. A procedure known as DC cardioversion can trigger the heart into re-establishing normal rhythm for a relatively short amount of time. However, around 70% of patients treated with DC cardioversion revert to exhibiting atrial fibrillation within one year of the DC cardioversion. Lastly, ablating the walls of the atrial chambers has been found to be effective. Ablation is the only currently known therapy that can achieve long term freedom from atrial fibrillation.

The cardiac ablation technique usually involves delivering a transvenous catheter, often via the groin, to the heart and applying energy to the catheter tip so as to ablate the inner heart walls. In other approaches an ablation device can be applied by a surgeon to the external walls of the cardiac chambers. In some types of atrial fibrillation ablation the posterior wall of the left atrium is electrically isolated using an ablating catheter or device. The aim of the surgeon performing the ablation procedure is to draw a "fence" with the catheter so as to create a line of ablation that prevents electrical signals from crossing the fence. An island of the atrial wall can be cut-off electrically from the rest of the heart by drawing a circle, square or triangle (or other closed shape) with the catheter to isolate an expanse of tissue.

The technique is difficult and requires surgical skill. The ablation is usually done while the heart is beating and the heart walls are slippery and irregular. If the ablation is done with a catheter having an ablating tip in the form of a point, then many point ablations need to be made in a line. Each point ablation typically takes 15-20 seconds to be made. Although the surgeon usually has x-ray fluoroscopy and 3D mapping visualisation available during the procedure, it is nevertheless difficult for the surgeon to be sure that an unbroken line of ablations has been created on the heart surface.

Once the ablation procedure has been completed, it is useful to know whether it was successful. This is particularly the case 2-3 months after the ablation has taken place. In some circumstances, some areas of heart tissue may "recover" so that the posterior wall of the left atrium is no longer electrically isolated, even though it was deemed isolated at the time of the ablation surgery.

The procedure for determining whether an ablation procedure was successful is not simple. Typically, a mapping catheter (usually having an electrode arranged in a spiral configuration) is passed up the femoral vein from the groin into the left atrium via an atrial transseptal puncture hole created in the heart by a steel needle. A pacing catheter is also inserted via the same route. Both the pacing catheter and the mapping catheter are then placed so as to contact the atrial wall at a location that is "inside" the area that the fence is supposed to surround. The pacing rate is selected to be above the natural rhythm of the heart. While inside the area of the fence, it would be expected that the mapping catheter is able to receive the electrical signals transmitted by the pacing catheter through the heart walls. It would also be expected that the heart does not adopt the pacing rate set, as the area being paced is supposed to be electrically isolated. The mapping catheter can then be moved to a location outside of the area surrounded by the fence and it can be determined whether electrical signals are able to cross the fence or not. If they cannot cross the fence (and the heart does not adopt the applied pacing), electrical isolation can be confirmed.

This procedure can be done either while under anaesthesia or when conscious. It represents a lengthy and highly invasive procedure with a potential risk of serious complications. Furthermore, it is an expensive procedure.

It would thus be desirable if there existed a way to determine the ablation condition that did not rely on expensive, invasive and risky surgical procedures.

SUMMARY OF THE DISCLOSURE

The present disclosure provides a method of determining heart ablation condition using an esophageal catheter.

In an exemplary embodiment, the method comprises inserting an elongate esophageal device comprising at least one electrode into a subject's esophagus, applying a predetermined pacing to one or more electrode(s) of the elongate esophageal device and monitoring the subject's heart rate to determine if the predetermined pacing is adopted by the heart.

It has been found that a device passed down the esophagus can be positioned so as to present one or more electrodes to be adjacent to a part of the esophageal lumen that is adjacent to the wall of the heart. An electrical pacing current can be applied to the electrode(s) and, in a normal unablated heart, this would cause the heart to pace at the pacing rate set by the pacing signal. However, if the heart wall has undergone ablation so as to isolate a portion of the wall, the esophageal pacing device will not cause the heart to pace. It is thus possible to determine whether the ablation surgery was successful or not using an esophageal device and by checking the patient's heart rate.

Specifically, in the event that the predetermined pacing is adopted by the heart, a determination can be made that the heart ablation was not effective. Similarly, in the event that the predetermined pacing is not adopted by the heart, it can be determined that the heart ablation was effective.

It is possible for the ablation checking procedure described here to be done within 15 minutes in a simple outpatient appointment. No organs or bodily surfaces are punctured and nothing needs to be placed inside the heart. Accordingly, the method described here represents a much simpler and less invasive procedure that is much less risky. It is also much quicker and much less expensive.

The elongate esophageal device can be an esophageal catheter comprising at least one electrode. Alternatively, it can be a transesophageal ultrasound probe that has been modified to include at least one electrode, for example by utilising a sheath around the probe that carries the at least one electrode.

For the method to be effective, the electrode(s) should be placed at a location where it/they would pace the heart. This means placing the electrode(s) at the level of the left atrium. This is possible through the use of a catheter or probe that has been calibrated for the specific patient, for example with markings that show when the catheter/probe has been inserted to the correct amount for the individual patient. More generally, the locating of the device can be ensured by using imaging, such as x-ray fluoroscopy imaging, to ensure that the electrodes are in the right position. If the device carries an ultrasound sensor, then this can be used to assist correct positioning of the electrode(s).

The pacing signal provided to the esophageal device should ideally be a signal that would cause pacing that is distinct from the patient's resting heart rate. Thus, the predetermined pacing is ideally performed with a frequency above the spontaneous heart rate of the subject.

It is most convenient if the pacing is set to be a value above the patient's heart rate, for example a frequency of between 70 and 150 pulses/minute, preferably between 80 and 120 pulses/min, more preferably between 90 and 110 pulses/min, most preferably around 100 pulses/min. The pacing pulses themselves can be of a duration ranging between 1 and 100 ms, but preferably between 5 and 20 ms and most preferably about 10 ms.

The pacing signal amplitude is set at a level whereby it can be ensured that the pacing signal will pass the esophageal lumen and reach the heart. Typically, the pacing signal has a current of between 1 and 60 mA, preferably between 10 and 30 mA, more preferably between 15 and 25 mA, most preferably around 20 mA.

The practitioner can determine whether the ablation condition is acceptable by noting whether the heart adopts the pacing rate applied to the esophageal pacing device. This can be checked through known measures such as a patient ECG monitor or, more simply, by checking the patient pulse.

This determination can also be automated by utilising a unit that receives a signal corresponding to the heart rate and compares it to the predetermined pacing rate. If the rates are the same, the unit can output a signal indicating that the heart has adopted the predetermined pacing. If the rates are different, the unit can provide an output signal indicating that the heart has not adopted the predetermined pacing. The unit can ideally receive the signal corresponding to the heart rate directly from an ECG monitor or other heart rate monitoring device.

In one aspect, the present disclosure includes the use of an esophageal electrocatheter for transesophageal pacing of the heart to determine the efficacy of a previously carried out heart ablation.

In a yet further aspect, the present disclosure includes a method of determining heart ablation condition, the method comprising inserting an esophageal device into a subject's esophagus, applying an electrical signal to the esophageal device at a location near to the heart, and monitoring the subject's heart to determine if the heart reacts to the electrical signal.

The esophageal device may comprise a flexible insertion element including an elongate member that terminates with a distal end. At or near the distal end one or more electrodes may be positioned to transmit an electrical pacing signal from outside of the body to the tissue in contact with the electrode. The esophageal device may include markings to indicate the distance from the point of insertion to the tip. This allows the position of the electrodes to be estimated in an individual patient. The esophageal catheter may include one or more markings or parts that show up when imaging, for example x-ray traceable parts. This allows the location of the electrode(s) to be monitored. These imagable parts can readily be implemented by using metal parts or by using x-ray dye. Indeed, the electrodes themselves can be configured to be x-ray traceable for example being made of platinum or steel.

The present disclosure also includes a system for determining a condition of a heart ablation previously formed in a subject, the system comprising an elongate esophageal device including a proximal end and a distal end, the distal end being configured for insertion into the esophagus of the subject, and an electrode; a pacing unit configured to apply an electrical pacing signal to the electrode; and a processing unit configured to compare a pacing rate of the electrical pacing signal and a heart rate of the subject to determine the condition of the heart ablation.

The processing unit is optionally configured to determine that the heart ablation is not effective if the heart rate of the subject adopts the pacing rate of the electrical pacing signal.

Similarly, the processing unit may be configured to determine that the heart ablation is effective if the heart rate of the subject does not adopt the pacing rate of the electrical pacing signal.

The system may comprise a monitoring unit configured to output an electrical signal indicative of the heart rate of the subject, and the processing unit may be configured to receive the electrical signal indicative of the heart rate of the subject.

The system may comprise an imaging unit configured to determine an in vivo location of the electrode(s).

The processing unit may be configured to determine, from the electrical signal indicative of the heart rate of the subject, a spontaneous heart rate of the subject; and said processing unit may be configured to control said pacing unit to output an electrical pacing signal that has a pacing rate different to said spontaneous heart rate.

This allows the system to automatically determine the patient's spontaneous heart rate, select an appropriate pacing rate, apply that pacing rate, determine if the heart adopts the rate, and provide an indication of whether the ablation procedure was successful. This may remove or reduce the need for the medical practitioner to select an appropriate pacing rate and to compare the ECG output with an output derived from the pacing unit.

The esophageal device can be positioned in the esophagus at the correct location using a variety of techniques. Visualisation, such as x-ray fluoroscopy can be used. If the device comprises an ultrasound transducer, then ultrasound imaging may be used. Knowledge of the distance between the subject's nose and left atrium can be used along with a scale on the catheter to ensure insertion to the correct depth. Known algorithms employing subject biometric data (e.g. subject height, distance from chin to sternum etc.) may be used to estimate the correct insertion depth of the device.

Additionally or alternatively, a method that uses the device as a heart sensor may be used. The natural heartbeats create naturally-occurring far-field electrical signals in and around the heart. These natural electrical signals can be picked up by the device electrode(s) and detected by a unit at the proximal end of the device. This unit may be the previously-mentioned processing unit. The detected naturally occurring signals can be analysed to indicate whether they are ventricular or atrial sensed signals. The signals can for example be sensed as the device is slowly inserted until the electrode is at a location close to the ventricular chamber (this will generally be the point of maximum ventricular signal). By then withdrawing the device from the point where ventricular signals are maximal by a predetermined amount, e.g. 4 cm, the correct positioning of the electrodes corresponding to the left atrium can be achieved without recourse to imaging.

The present disclosure thus also comprises a method of inserting an esophageal device into a subject, sensing electrical activity using an electrode on the device during insertion, determining an insertion depth that corresponds to the electrode being adjacent the ventricular chamber, and withdrawing the device a predetermined amount to position the electrode adjacent the atrial chamber.

The present disclosure further comprises an esophageal catheter having a distal end, said esophageal catheter comprising greater than 5 electrodes arranged along the distal end. Optionally, the catheter includes greater than 7 electrodes or greater than 9 electrodes arranged along the distal end. The electrodes may be spaced apart from a neighbouring electrode by a distance of between 4 and 50 mm, for example by 10 to 30 mm.

BRIEF DESCRIPTION OF THE DRAWINGS

The present disclosure will be described, by way of non-limitative example only, with reference to the accompanying drawings, in which.

DETAILED DESCRIPTION OF THE EMBODIMENTS OF THE DISCLOSURE

Figure 1:
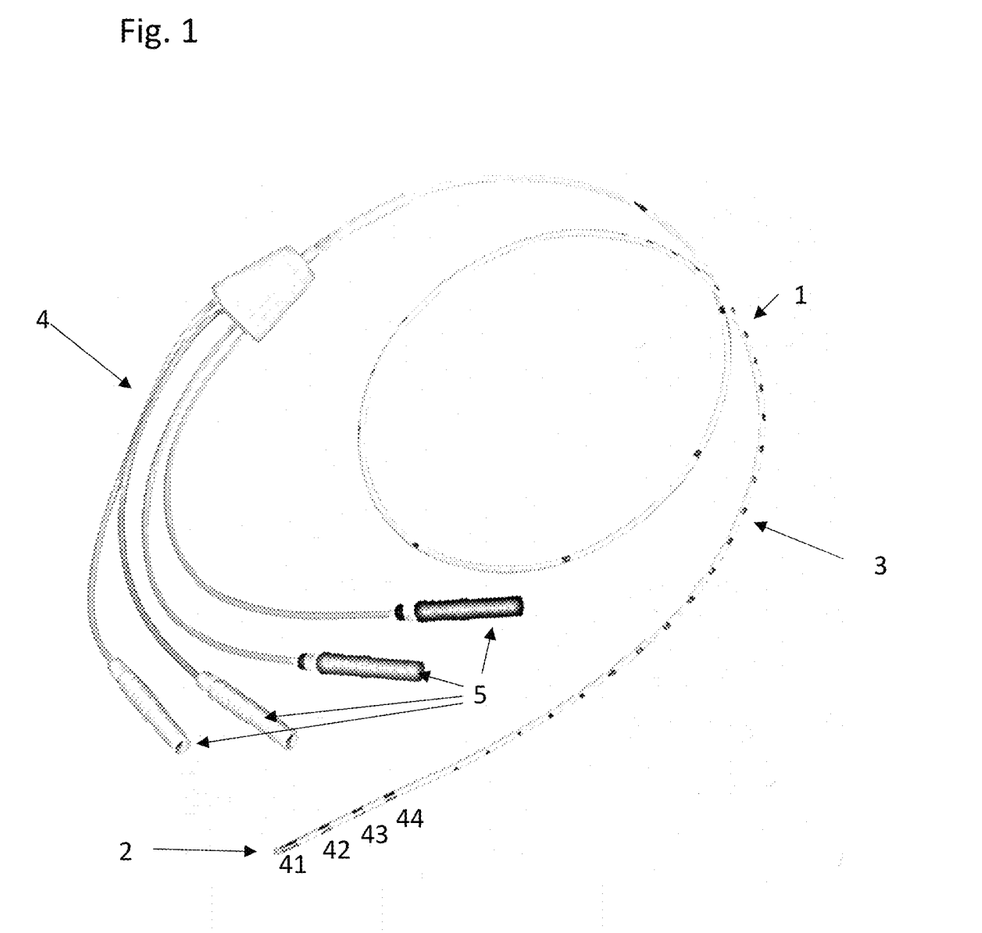
FIG. 1 shows a schematic view of an esophageal catheter that can be used in the present disclosure.

FIG. 1 shows an example of a device that can be used in systems and methods according to the present disclosure. The device is in the form of an esophageal catheter 1. The catheter 1 comprises a flexible insertion element, which includes an elongate member 3 that terminates with the distal end 2.

The distal end 2 comprises four electrode poles. Electrode 41 is located at or near the distal tip. Electrode 44 is located the most proximally of the four electrodes. There are two central electrodes labelled 42 and 43. The electrodes allow electrical signals to be transmitted from tissue they make contact with to the proximal end of the catheter. They also allow electrical signals at the proximal end to be transmitted to the tissue that they contact.

The esophageal catheter shown in FIG. 1 is commercially available from the company Fiab SpA as the Esoflex 4S esophageal diagnostic and pacing lead. While the Esoflex 4S catheter has been proven to be especially effective, any esophageal pacing device may be used. A similar, but not identical, catheter is shown in U.S. Pat. No. 8,145,289, hereby incorporated by reference in its entirety.

Figure 2:
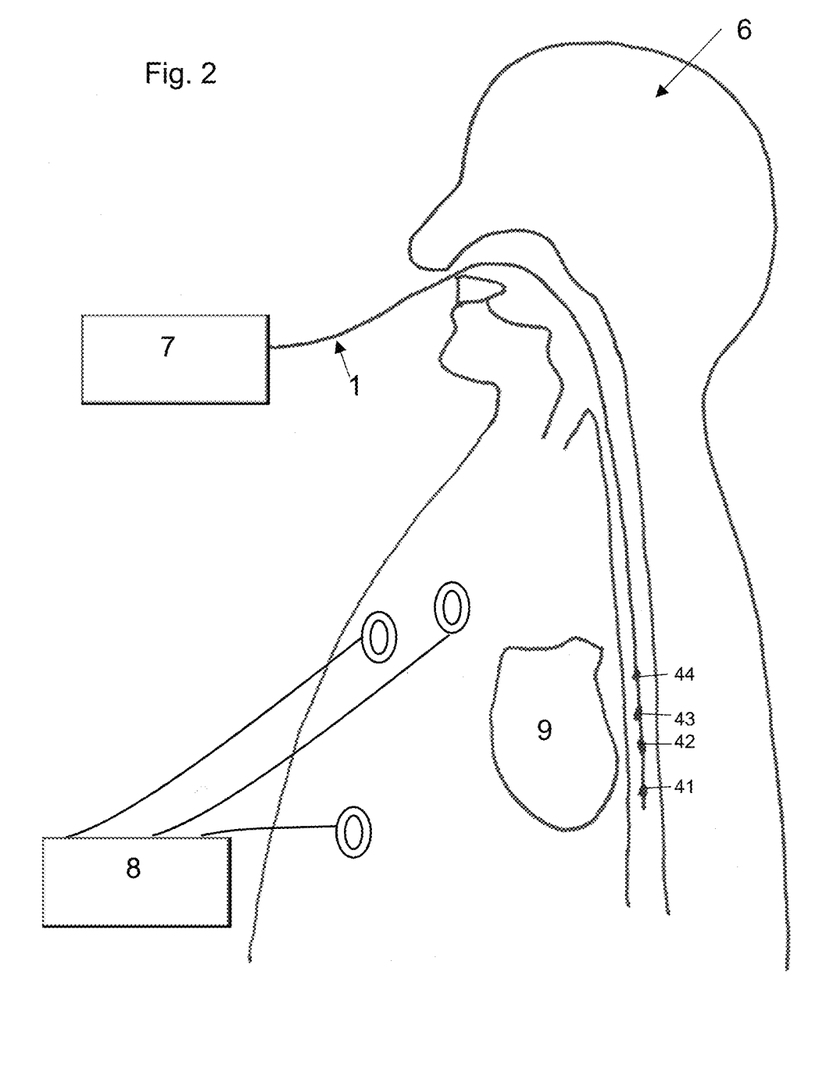
FIG. 2 shows a first embodiment of the system of the present disclosure.
Figure 3:
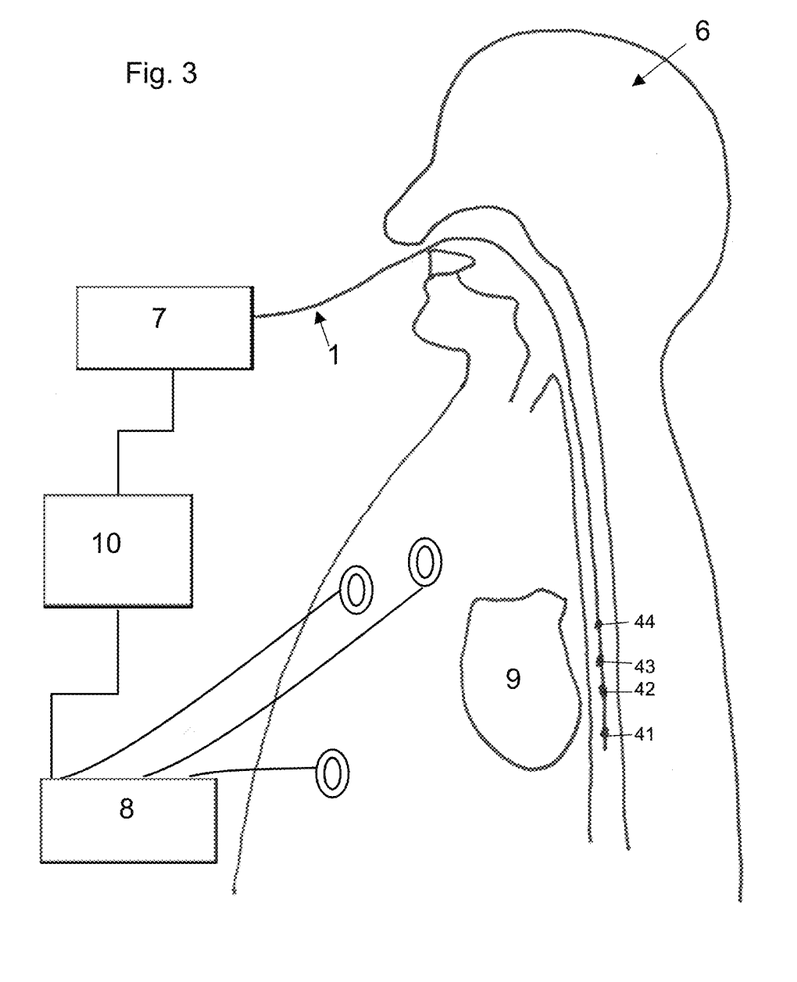
FIG. 3 shows a second embodiment of the system of the present disclosure.

The Esoflex 4S catheter comprises four pacing electrodes 41, 42, 43 and 44. Each electrode is connected via cables 4 which run inside the elongate member 3 and terminate outside it with connectors 5 for connection to an external unit that is not shown in FIG. 1. The external unit is shown in FIGS. 2 and 3 as unit 7. A Fiab 2007 (or similar) device may be used as external unit 7.

Although four electrodes are shown in FIG. 1, the present disclosure does not necessarily need to utilise four electrodes. Pacing can in principle be carried out with a single electrode, with the potential difference being applied between the electrode and an indifferent electrode patch somewhere on the subject's body. More simply, pacing can be carried out using two electrode poles on the catheter. Accordingly, not all of the electrodes shown in FIG. 1 need be used or need be present. The disclosure could be carried out with a catheter comprising just two electrodes or just one electrode with an indifferent electrode elsewhere in the body. Similarly, as disclosed later, several electrodes may be used as part of the disclosure.

The present disclosure uses the esophageal catheter to apply a pacing pulse train to the lumen of the esophagus at a position that is close to the heart. Any of the electrodes 41, 42, 43 or 44 may be used for this purpose. Ideally, two adjacent central electrodes for example 42 and 43 are used to apply the pacing. Once applied, the pacing pulse train will be transmitted across the lumen walls to the heart and, if the heart has not been ablated or has not been correctly ablated, will cause the heart to adopt the provided pacing.

The medical practitioner is able to determine whether the heart has adopted the supplied pacing either by taking the subject's pulse or by using a conventional monitor such as an ECG monitor. If the heart adopts the supplied pacing, then this indicates that the ablation technique was not fully successful. If, on the other hand, the heart does not adopt the supplied pacing, then this shows that the ablations in the heart are effective in isolating the electrical pacing signal. This therefore constitutes an indication that the ablation procedure was successful.

FIG. 2 shows a first embodiment of the system being used in a procedure on a subject 6 (e.g., a patient). The esophageal device, e.g. catheter 1, is shown inserted into the subject's esophagus via the nose. It is entirely viable to use the mouth instead of the nose if desired. The catheter 1 is shown connected to a pacing unit 7. The subject 6 is shown connected to an ECG monitor 8 via three leads. The ECG monitor 8 may include a display (not shown) which outputs a signal corresponding to the subject's heart activity. Any device for measuring the subject's pulse may be used instead of the ECG monitor 8.

The pacing unit 7 is able to apply a predetermined pacing rate to the electrode(s) of the esophageal character 1. This pacing is preferably one that is distinct from the subject's own heart rate. Thus, for the typical case where the subject 6 has a spontaneous heart rate of around 70 pulses/min, the pacing unit 7 may be set to pace at a rate of around 100 pulses/min. In general, any rate that is different to the subject's heart rate will be useful, and this may typically lie in the range of between 70 and 150 pulses/min, more preferably between 90 and 110 pulses/min.

The pacing unit is also ideally configured to deliver pulses with a current of between 1 and 100 mA, preferably between 5 and 35 mA. If the current is lower than 5 mA, then it may be difficult to be sure that the pacing pulses have traversed the esophagus and have reached the heart 9. If the current is greater than 35 mA, this may cause discomfort for the subject 6. More preferably, the pacing current is controlled to be between 15 and 25 mA, even more preferably around 20 mA.

The esophageal device is inserted into the subject's esophagus such that one or more of the electrodes 41, 42, 43, 44 lie in the lumen of the esophagus adjacent to the myocardial wall of the heart 9, preferably adjacent to the left atrium of the heart. In this position, the pacing pulses will cross the esophagus into the heart 9, preferably arriving first in the area of the posterior wall of the left atrium.

The medical practitioner before performing the method of the present disclosure monitors the output of the ECG monitor 8 to determine the subject's spontaneous heart rate. Thereafter, the pacing unit 7 is activated to apply a pacing that is different to the subject's heart rate. The medical practitioner is thereafter able to readily determine, for example by consulting the monitor 8, whether the heart has adopted the pacing supplied by the pacing unit 7, or not. In the event that the heart adopts the pacing, this is a sign that the ablation technique has not been completely effective. In the event that the heart does not adopt the pacing, this is a sign that the ablation procedure has been effective.

A second embodiment is shown in FIG. 3 of the drawings. In this embodiment, the pacing unit 7 is connected to a processing unit 10. This processing unit 10 is connected to the monitoring unit 8. According to this embodiment, the pacing unit 7 supplies to the processing unit 10 a signal indicative of the predetermined pacing signal. Further, the monitoring unit 8 supplies to the processing unit 10 a signal indicative of the subject's heart rate. The processing unit 10 is configured to compare the predetermined pacing signal with the subject's heart rate and make a determination of whether the heart has adopted the pacing or not. This saves the medical practitioner from the necessity to study and compare the output of the monitoring unit 8 with the pacing signal that has been configured by the pacing unit 7. The processing unit may be connected to a display to provide the comparison result, or may output an audible sound or give any other indication.

This embodiment also has a further advantageous mode. The monitoring unit 8 can be used to automatically measure the spontaneous subject heart rate prior to the method of the present disclosure being carried out. This spontaneous pre-test heart rate can be supplied by the monitoring unit 8 to the processing unit 10. Thereafter, the processing unit 10 may select an appropriate pacing rate. For example, this could be selected to be 30 pulses/min higher than the spontaneous subject heart rate. For example, if the measured initial spontaneous heart rate is 70 pulses/min, the processing unit will select a predetermined pacing rate of 100 pulses/min. The processing unit 10 may thereafter specify this pacing rate to the pacing unit 7 and the pacing unit 7 may be configured to take this specified rate as the pacing rate to be applied. Thereafter, this mode works in the same manner as the second embodiment with the processing unit 10 performing a comparison to determine whether the heart has adopted the pacing rate or not. The additional advantage of this mode is that the system automatically selects a pacing rate that is different to the subject's starting heart rate. This again saves the medical practitioner time and effort.

The pulses provided by the pacing unit 7 may have any practical duration and pulse shape, but typically have a duration of 1-100 ms, more preferably around 10 ms. In all of the embodiments described, the predetermined pacing can be carried out for a relatively short period of time, for example about 10-15 seconds, to demonstrate a capture or lack of capture by the heart of the pacing. Thus, once the device has been inserted and positioned in the esophagus, the method is very quick to carry out.

Prior to carrying out the above-described methods, it is necessary to insert the device to a depth where an electrode is adjacent to the part of the heart to be tested, usually the left atrium. As noted above, an esophageal catheter can be positioned in the esophagus at the correct location using a variety of techniques. Visualisation, such as x-ray fluoroscopy or 3D mapping can be used. Knowledge of the distance between the subject's nose (or mouth) and left atrium can be used along with a scale on the catheter to ensure insertion to the correct depth. The distance between the nose/mouth and the left atrium can be estimated, for example by using empirical algorithms based on a measurement of the subject's height or chin to sternum dimension for example. Additionally or alternatively, a method that uses the catheter as a heart sensor may be used.

The subject's natural heartbeats create naturally-occurring far-field electrical signals in and around the heart. These natural electrical signals can be picked up by the esophageal device electrode(s) and detected by a unit at the proximal end of the device. This unit may be the previously-mentioned processing unit 10. In this case the processing unit 10 may include signal processing functionality. The detected naturally occurring signals can be analysed, preferably by the processing unit 10, to indicate whether they are ventricular or atrial sensed signals—this can be done by looking at the characteristics of the signals such as the pulse shape and timing. Additional accuracy can be obtained by simultaneously looking at the output of the monitoring device 8 and thereby deriving how the signals detected by the electrode(s) correspond to the heart beat signals of the subject. The processing unit 10 is ideally configured to carry out the necessary comparison and analysis automatically. One electrode may be used for the sensing, although such sensing could be done at more than one electrode simultaneously.

The signals can in a first example be sensed as the device is slowly inserted into the esophagus. As the device is inserted so that the electrode passes the ventricular chamber, the signal will peak and then diminish. By inserting the device to a depth where the signal is maximised, it can be deduced that the electrode is at a location close to the ventricular chamber (this will generally be the point of maximum ventricular signal). By then withdrawing the device from the point where ventricular signals are maximal by a predetermined amount, e.g. 4 cm, the correct positioning of the electrode(s) adjacent to the left atrium can be achieved without recourse to imaging. This procedure of deducing the atrial chamber position with reference to the ventricular chamber position is generally useful because if the subject has undergone ablation of the left atrial chamber, the signals emitted by that chamber will be weak or non-existent. It is thus in general not possible to determine directly the signals emitted by the ablated atrial chamber itself.

The present disclosure thus also comprises a method of inserting an esophageal device into a subject, sensing electrical activity using an electrode on the device during insertion, determining an insertion depth that corresponds to the electrode being adjacent the ventricular chamber, and withdrawing the device a predetermined amount to position the electrode adjacent the atrial chamber.

Furthermore, the processing unit 10 of the present disclosure may be configured to sense electrical signals as the device is inserted, and may be configured to provide an indication of when the electrode(s) is/are adjacent the ventricular chamber.

In some embodiments, the processing unit 10 may take the form of a general purpose or special purpose computer, or any other suitable computing device. For example, the processing unit 10 may be a programmable logic controller, a desktop computer, a laptop computer, a tablet computer, a smartphone, a server, or some combination thereof. The processing unit need not be a standalone device, and may be incorporated into the pacing unit 7, the monitoring unit 8, the catheter, or distributed across multiple devices. In some embodiments, the processing unit 10 may include a processor (e.g., a microprocessor), a memory, a communication interface, an analog-to-digital converter, a user interface, and a system bus enabling the processor to communicate with the other components of the processing unit 10. The memory may include a non-transitory computer-readable storage medium configured to store data, including, for example, non-transitory computer-readable instructions constituting one or more services or programs and any data operated on or produced by such services or programs. The memory may store the data on a volatile (e.g., RAM) and/or non-volatile memory (e.g., a hard disk), and may be a removable or non-removable memory. The processor may be configured to fetch and execute the instructions stored in the memory in order to perform various functions of the methods disclosed herein, including, for example, comparing the pacing rate of the electrical pacing signal of the pacing unit 7 and the heart rate of the subject detected by the monitoring unit 8 in order to determine the condition of the heart ablation. The user interface may include a graphical display (e.g., an LED monitor, a touchscreen, etc.), an input unit (e.g., a keypad, a keyboard, buttons, knobs, etc.), lights, and/or a speaker. In some embodiments, executing the instructions stored in the memory may cause the processor to control the user interface to display an indication (e.g., text, symbol, colored or flashing light, etc.) and/or generate a sound signifying the condition of the heart ablation. The analog-to-digital converter may be configured to receive analog signals received from the electrodes 41, 42, 43, 44 the pacing unit 7, and/or the monitoring unit 8, convert these analog signals into digital signals, and transmit the digital signals to the processor for analysis. The communication interface may be configured to establish communication via a network and may include an antenna for wireless communications, a port for a wired connection, a connection to a modem, a connection to a router, or some combination thereof.

Furthermore, in some embodiments, the processing unit 10 may not include a physical processor and may be configured as a program module consisting of a set of non-transitory computer-readable instructions to be executed by a processor of a computing device on which the program module is installed.

Figure 4:
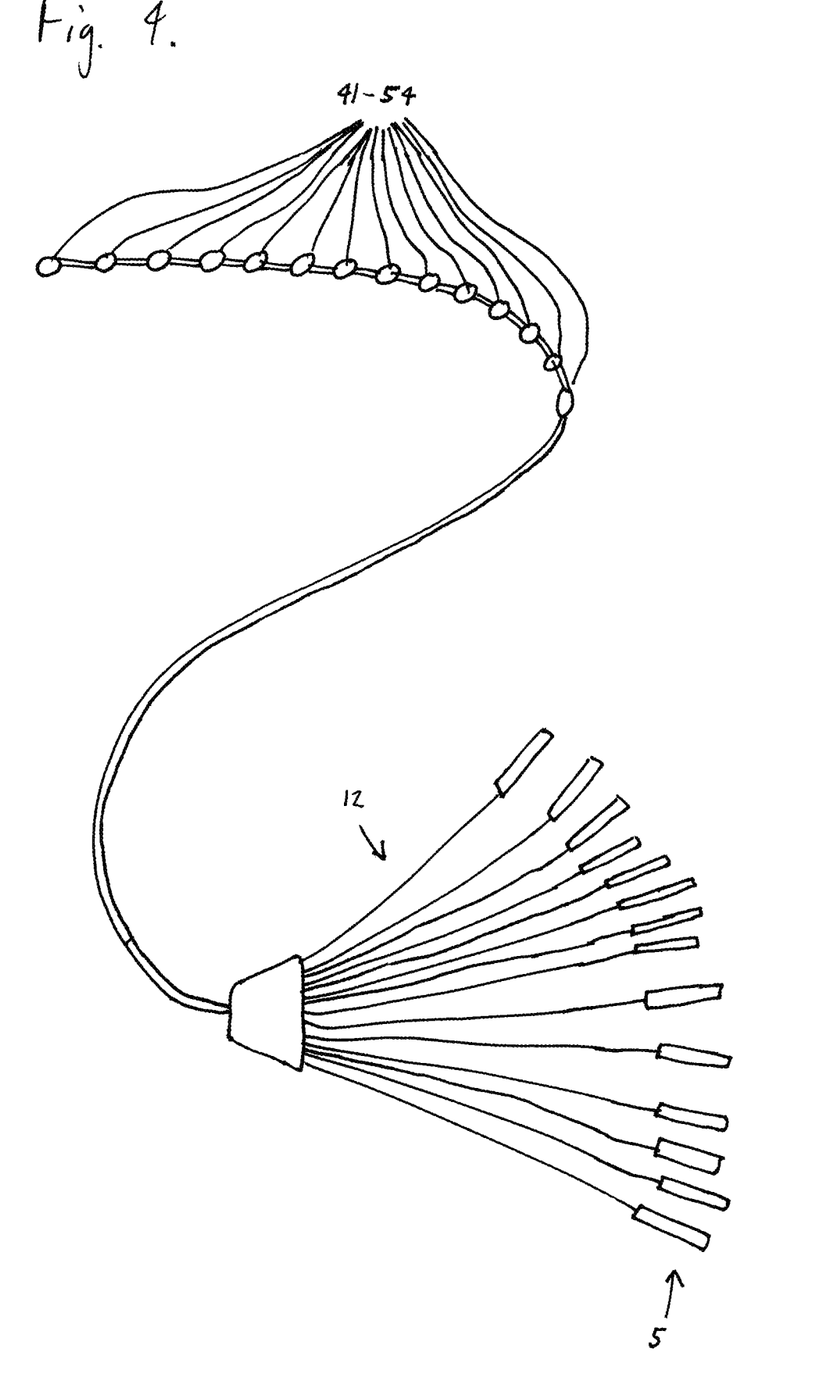
FIG. 4 shows a catheter configuration according to one embodiment of the disclosure.

FIG. 4 shows a catheter arrangement according to a further embodiment of the present disclosure. This catheter has several electrodes, preferably more than 5 electrodes, arranged along the distal end. Each electrode in the series 41-54 is capable of transmitting a signal to a connecting cable array 12, and thereon to connectors 5. According to this embodiment, the catheter may be inserted a predetermined amount, e.g. 50 cm, and any naturally occurring heart beat signals may be sensed by several of the electrodes, either simultaneously or at separate time points. It can then be derived which one of the distal electrodes 41-54 is closest to the ventricular chamber. This allows a deduction of where the atrial chamber is, for example by deducing that the atrial chamber is 4 cm above the location of the electrode that has the strongest signal or for example 3 cm above the transition point from ventricular to atrial signals of greatest amplitude. Thereafter, the electrode closest to the atrial chamber (eg. the electrode that is 4 cm above the electrode that exhibited the strongest signal) may be used for supplying the predetermined pacing in accordance with the above embodiments. This allows the catheter to be positioned without needing to image or repeatedly insert/withdraw the catheter, and allows the pacing to be delivered to the correct location to optimally determine heart ablation condition. The catheter useful in the method preferably has greater than 5 electrodes, more preferably greater than 8 electrodes, still more preferably greater than 10 electrodes, and yet more preferably greater than 13 electrodes. The example illustrated in FIG. 4 has 14 electrodes spaced apart from their neighbour by a distance of around 1 cm. The electrodes may be spaced apart by a distance in the range 4 to 50 mm, and may be regularly or non-regularly spaced.

It is possible to use ultrasound technology in the disclosed methods and apparatus. Specifically a catheter comprising an ultrasound transducer may be used. The ultrasound transducer may be located near to an electrode of the catheter and will allow ultrasound images of the tissues near to the electrode top be obtained. The medical practitioner is able to identify heart structures in the ultrasound image, for example it is possible to identify a fluid-filled chamber anterior to the transducer (rather than the solid tissue of the mediastinum or the air-filled space of the trachea). Ultrasound imaging may be used alternatively or additionally to the other methods described above.

Another way to use ultrasound imaging is to start from a transesophageal echocardiography probe and apply one or more pacing electrodes to it. The electrodes can conveniently be located in a thing flexible sheath that surrounds the probe. Such a device allows imaging and positioning with the ultrasound transducer and allows pacing and sensing with the one or more electrodes.

Example Study

A study on 22 subjects has been carried out to show the effectiveness of the methods, apparatus and systems according to the present disclosure. An esophageal catheter was passed down the esophagus and positioned to lie behind the left atrium. An x-ray fluoroscopy table was used to aid in the positioning. Stimulation was carried out over a range of different currents with 10 ms pulse widths. It was found in all cases where previous procedures had not already isolated the posterior wall of the left atrium that the heart adopted the supplied pacing with a current set at around 20 mA and a frequency at around 100 pulses/min.

Thereafter, a number of these patients underwent an ablation procedure. This involved ablating the inner surfaces of the left atrium wall resulting in electrical isolation of the posterior wall of the left atrium. Isolation of this region was confirmed by pacing and sensing within the ablated area using catheters within the atrial chamber using the standard technique.

The esophageal catheter was then once again used to supply a pacing signal at around 20 mA, 10 ms pulse duration and 100 pulses/min. It was found in all cases that the heart did not adopt the pacing after the ablation technique had been carried out successfully. This demonstrated that the esophageal catheter is capable of pacing a heart that has not been ablated but will not pace a heart that has been properly ablated (i.e., where the intended region has been electrically isolated). This therefore demonstrates the suitability of esophageal catheters for determining heart ablation condition.

The study was carried out with 22 individuals. Typically, it was necessary to insert the esophageal catheter through the nose to a depth of between 40 and 50 cm.

For future clinical use, the ideal timepoint for performing the presently disclosed testing method may correspond to the end of the "blanking period", that is, approximately 2 to 3 months after the ablation procedure has taken place.

What is claimed is:

1. A method of determining a condition of a previously established heart ablation, said method comprising:
   inserting an elongate esophageal device comprising an electrode into an esophagus of a subject whose heart possesses the previously established heart ablation;
   applying a predetermined pacing to the electrode of the elongate esophageal device;
   monitoring a heart rate of the subject to determine if the predetermined pacing is adopted by a heart of the subject; and
   in the event that the predetermined pacing is not adopted by the heart, determining that the heart ablation is effective.

2. The method of claim 1, further comprising:
   after inserting the elongate esophageal device into the esophagus and before applying the predetermined pacing to the electrode, positioning the electrode of the device in the esophageal lumen at a location adjacent the myocardial wall of the heart.

3. The method of claim 2, comprising imaging an area including the device electrode and the heart.

4. The method of claim 3, wherein said imaging comprises X-ray fluoroscopy.

5. The method of claim 2, wherein the electrode of the device is positioned in the esophageal lumen at a location adjacent the left atrium of the heart.

6. The method of claim 1, wherein said predetermined pacing is performed with a current of between 5 and 35 mA.

7. The method of claim 6, wherein said predetermined pacing is performed with a current of between 15 and 25 mA.

8. The method of claim 1, wherein said predetermined pacing is performed with a frequency of between 70 and 150 pulses/minute.

9. The method of claim 8, wherein said predetermined pacing is performed with a frequency of between 90 and 110 pulses/minute.

10. The method of claim 1, further comprising:
    in the event that the predetermined pacing is adopted by the heart, determining that the heart ablation is not effective.

11. The method of claim 1, wherein said predetermined pacing is performed with a frequency above a spontaneous heart rate of the subject.

12. The method of claim 1, wherein a unit is provided that receives a signal corresponding to the heart rate and compares the signal to the predetermined pacing so as to provide a signal indicative of whether the heart has adopted the predetermined pacing or not.

13. A method of determining a condition of a previously established heart ablation, said method comprising:
    inserting an esophageal device into an esophagus of a subject whose heart possesses the previously established heart ablation;
    applying an electrical signal to the esophageal device at a location near to the heart of the subject;
    monitoring the heart of the subject to determine if the heart reacts to the electrical signal; and
    in the event that the heart does not react to the electrical signal, determining that the heart ablation is effective.

14. The method of claim 13, wherein monitoring the heart of the subject to determine if the heart reacts to the electrical signal comprises comparing a predetermined pacing rate of the electrical signal to a heart rate of the subject.

* * * * *